United States Patent
Branquinho Gomes et al.

(10) Patent No.: US 11,917,567 B2
(45) Date of Patent: Feb. 27, 2024

(54) METHOD AND DEVICE FOR SYNCHRONIZING DATA PACKETS FROM EMBEDDED DATA SENSORS MONITORING BODY MOTION OF A PATIENT

(71) Applicant: Sword Health, S.A., Oporto (PT)

(72) Inventors: André Branquinho Gomes, Aveiro (PT); Ana Clara Ferreira Matos, S. João da Madeira (PT); Luis Ungaro Pinto Coelho, Vila Nova de Gaia (PT); Virgílio António Ferro Bento, Oporto (PT)

(73) Assignee: SWORD HEALTH, S.A., Oporto (PT)

( * ) Notice: Subject to any disclaimer, the term of this patent is extended or adjusted under 35 U.S.C. 154(b) by 565 days.

(21) Appl. No.: 17/250,091

(22) PCT Filed: May 22, 2019

(86) PCT No.: PCT/EP2019/063267
§ 371 (c)(1),
(2) Date: Nov. 23, 2020

(87) PCT Pub. No.: WO2019/224279
PCT Pub. Date: Nov. 28, 2019

(65) Prior Publication Data
US 2021/0212008 A1    Jul. 8, 2021

(30) Foreign Application Priority Data

May 25, 2018  (PT) .......................................... 110760
May 29, 2018  (EP) .................................... 18174960

(51) Int. Cl.
*H04W 56/00* (2009.01)
*G16H 40/40* (2018.01)
(Continued)

(52) U.S. Cl.
CPC ....... *H04W 56/0015* (2013.01); *A61B 5/0024* (2013.01); *G16H 40/40* (2018.01); *G16H 40/63* (2018.01); *H04W 56/002* (2013.01)

(58) Field of Classification Search
CPC .......... H04W 56/0015; H04W 56/002; G16H 40/40; G16H 40/63; A61B 5/0024
See application file for complete search history.

(56) References Cited

U.S. PATENT DOCUMENTS

| | | |
|---|---|---|
| 11,372,484 B2 | 6/2022 | Branquinho Gomes et al. |
| 11,609,102 B1 | 3/2023 | Santos et al. |

(Continued)

FOREIGN PATENT DOCUMENTS

| | | |
|---|---|---|
| EP | 3586745 A1 | 1/2020 |
| PT | 110804 A | 12/2019 |

(Continued)

OTHER PUBLICATIONS

International Search Report and Written Opinion for PCT/EP2019/063267 dated Jul. 17, 2019.

(Continued)

*Primary Examiner* — Elton Williams
(74) *Attorney, Agent, or Firm* — SCHWEGMAN LUNDBERG & WOESSNER, P.A.

(57) ABSTRACT

Method for synchronizing data packets is disclosed, which includes: receiving an initial data packet having a timestamp from a first sensor; storing the timestamp of the initial data packet from the first sensor, herewith defined as reference timestamp; for each received data packet having a timestamp from said sensors, received subsequently to said initial data packet, for the first sensor, storing the timestamp of the most recent data packet from said first sensor, herewith defined as reference timestamp; for the sensors other than the first sensor, calculating the difference between the (Continued)

timestamp of a received data packet and the reference timestamp; calculating an average of said differences for the received data packets for each said sensor; correcting the timestamp of the received data packet with the calculated average of said differences of the respective sensor; using the corrected timestamps to synchronize the data packets from the embedded wireless data sensors.

20 Claims, 5 Drawing Sheets

(51) Int. Cl.
*G16H 40/63* (2018.01)
*A61B 5/00* (2006.01)

(56) References Cited

U.S. PATENT DOCUMENTS

| | | | |
|---|---|---|---|
| 11,720,185 | B2 | 8/2023 | Branquinho Gomes et al. |
| 11,726,165 | B1 | 8/2023 | Santos et al. |
| 2010/0014460 | A1 | 1/2010 | Shin et al. |
| 2017/0013572 | A1 | 1/2017 | Jayaraman et al. |
| 2020/0005926 | A1 | 1/2020 | António Ferro Bento et al. |
| 2023/0003528 | A1 | 1/2023 | Santos et al. |
| 2023/0003863 | A1 | 1/2023 | Alves et al. |
| 2023/0166155 | A1 | 6/2023 | Coelho Alves et al. |

FOREIGN PATENT DOCUMENTS

| | | | | |
|---|---|---|---|---|
| WO | WO-2014174117 | A1 | * 10/2014 | ......... A61B 5/14532 |
| WO | WO 2018/013569 | | 1/2018 | |
| WO | WO-2019224279 | A1 | 11/2019 | |
| WO | WO-2019243438 | A1 | 12/2019 | |
| WO | WO-2020049097 | A1 | 3/2020 | |
| WO | WO-2020115251 | A1 | 6/2020 | |
| WO | WO-2020127246 | A1 | 6/2020 | |
| WO | WO-2020139093 | A1 | 7/2020 | |
| WO | WO-2020200891 | A1 | 10/2020 | |
| WO | WO-2020221704 | A1 | 11/2020 | |
| WO | WO-2020249514 | A1 | 12/2020 | |
| WO | WO-2021048022 | A1 | 3/2021 | |
| WO | WO-2021089407 | A1 | 5/2021 | |
| WO | WO-2021130324 | A1 | 7/2021 | |
| WO | WO-2021180869 | A1 | 9/2021 | |
| WO | WO-2021259688 | A1 | 12/2021 | |
| WO | WO-2022167582 | A1 | 8/2022 | |
| WO | WO-2022207485 | A1 | 10/2022 | |

OTHER PUBLICATIONS

Espina et al., "Wireless Body Sensor Network for Continuous Cuff-less Blood Pressure Monitoring", *Proceedings of the 3$^{rd}$ IEEE-EMBS International Summer School and Symposium on Medical Devices and Biosensors*, Nov. 15, 2006.

Min et al., "Time synchronization in Wireless Physiological Information Sensor Network", *Proceedings of the 2005 IEEE Engineering in Medicine and Biology 27$^{th}$ Annual Conference*, 5176-5178, 2005.

* cited by examiner

METHOD AND DEVICE FOR SYNCHRONIZING DATA PACKETS FROM EMBEDDED DATA SENSORS MONITORING BODY MOTION OF A PATIENT

CROSS-REFERENCE TO RELATED APPLICATIONS

This application is a national phase application under 35 U.S.C. § 371 of International Application No. PCT/EP2019/063267 filed May 22, 2019, which claims the benefit of priority of Portuguese Patent Application No. 110760 filed May 25, 2018, and European Patent Application No. 18174960.7 filed May 29, 2018. The referenced applications are incorporated into the present application by reference.

TECHNICAL FIELD

The present disclosure relates to a method and device for synchronizing data packets from embedded data sensors monitoring body motion of a patient, in particular data packets transmitted by a Bluetooth protocol by embedded data sensors monitoring body motion of a patient.

BACKGROUND

Data packets from embedded data sensors present difficulties in synchronization, in particular data packets transmitted by a Bluetooth protocol from embedded data sensors.

Devices for keeping an accurate time basis across a plurality of embedded data sensors, can be costly, battery-intensive consumers and are usually burdensome to maintain configured and in synchronization.

Synchronization of time-sensitive sensors can be ensured by using cables with a timing signal, but for wireless sensors this is not possible.

Document US2017013572 discloses a system for discovering and synchronizing nodes that communicate wirelessly with directional antennas, which causes a first node to communicate a timestamp of the first node to each neighbouring node of the first node and to cause each neighbouring node to communicate the timestamp of the first node to each other neighbouring nodes of the neighbouring node, wherein nodes synchronize their respective timestamps upon receipt of the timestamp of the first node, wherein communicating the timestamp continues until each node in the network has been synchronized to the timestamp of the first node.

Document US2017013572, however, requires complex time keeping equipment and requires nodes to synchronize between themselves.

Inadequate synchronization creates problems in interpreting data body motion because body motion data, obtained from a plurality of embedded data sensors needs to be analysed in parallel, to obtain meaningful scrutiny, for example with a same event present in concurrent data streams requiring to be analysed from those data streams at a simultaneous point corresponding to that event in time. The simultaneous point can be obtained by adequate calculations, but some or most communications protocols do not provide a common time reference or for easily synchronizing the time references of the individual devices.

For example, the Bluetooth protocol does not explicitly allow a simple straightforward synchronism mechanism. When transmitting, for example, up to 50 packets/second one gets into difficult synchronization issues using Bluetooth protocol. Also, the Bluetooth stack has a single queue mixing all sensors, but this is not even the worst problem—one of the main problems is the lack of a global time reference.

These facts are disclosed in order to illustrate the technical problem addressed by the present disclosure.

GENERAL DESCRIPTION

The present disclosure relates to a method and device for synchronizing data packets from embedded data sensors monitoring body motion of a patient, in particular data packets transmitted by a Bluetooth protocol. Embedded sensors are sensors placed in a patient that interact with the patient to measure therapeutically important parameters like displacement, angle, temperature, strength, speed, among others. These embedded computers, or sensor nodes, are often physically small, relatively inexpensive computers, each with some set of sensors or actuators According to an aspect of the disclosure, an embedded data sensor system comprises several embedded data sensors, for example orientation sensors (said sensors being also called trackers), each being a data packet generator and emitter, and a data packet receiver (for example, a mobile device or a tablet) that is responsible for data packet processing.

The receiver needs synchronized data packets from the different sensors or trackers in order to correctly assess human motion, for example for rehabilitation purposes in real time.

Such a device may be assumed to be characterized by the following features and issues.

Data packets are generated by each sensor or tracker with a fixed period.

Data packets are usually received by the receiver in bursts, so the fixed period is not maintained during reception. This one of the sources of synchronization difficulties.

The receiver normally does not receive a packet from a given sensor or tracker older than the last received packet from that same sensor or tracker.

Data packets typically contain a quaternion (4 numeric values that describe a rotation, typically 4 real-arithmetic numbers).

Data packets come with a timestamp (internal to each tracker), hereafter defined as raw timestamp.

This raw timestamp may be used to know the time interval between two generated packets (between the time instants where they were created) for the same sensor or tracker, but the raw timestamps from different trackers do not have any type of synchronization as the initial timestamp base for each sensor or tracker will differ.

Typically, sensors or trackers do not initiate operation and start sending packets to the tablet at the same time, causing the initial timestamp base for each sensor or tracker to be different.

Typically, packets are occasionally lost, i.e. they may not be received (e.g. connection problems) by the receiver.

It is disclosed a method for synchronizing data packets from embedded wireless data sensors for monitoring body motion of a patient, wherein each said sensor has an independent time base for applying timestamps to data packets sent from each said sensor with a respective sensor measurement; said method comprising the steps of:
  receiving an initial data packet having a timestamp from a sensor herewith defined as first sensor;
  storing the timestamp of the initial data packet from the first sensor, herewith defined as reference timestamp;

for each received data packet having a timestamp from said sensors, received subsequently to said initial data packet, for the first sensor, storing the timestamp of the most recent data packet from said first sensor, herewith defined as reference timestamp;

for the sensors other than the first sensor, calculating the difference between the timestamp of a received data packet and the reference timestamp;

calculating an average of said differences for the received data packets for each said sensor; correcting the timestamp of the received data packet with the calculated average of said differences of the respective sensor;

using the corrected timestamps of the received data packets to synchronize the data packets from the embedded wireless data sensors.

The method is carried out by means of a device comprising an electronic data processor that receives the data packets having a timestamp from the embedded wireless data sensors, including the initial data packet of the first sensor. The device processes the received data packets so as to store the timestamp of the most recent data packet received from the first sensor; the device calculates the difference between the timestamp of data packets received from the sensors other than the first sensor and the reference timestamp (i.e. the timestamp of the most recent data packet received from the first sensor), calculates the average and corrects the timestamp of said received data packets from the sensors other than the first sensor. The device synchronizes the received data packets by using the corrected timestamps thereof, that is, the data packets received from sensors other than the first sensor. For monitoring the body motion of the patient, the device attains said synchronization by processing the data packets received from each sensor (i.e. including the data packets received from the first sensor) that have a timestamp difference, with respect to the data packets from the other sensors, that is lower than the predetermined accepted maximum. Accordingly, in each period the device processes one sensor measurement from all sensors when the timestamp of the data packet of the first sensor and the corrected timestamp of the data packets of the sensors other than the first sensor have a difference lower than the predetermined accepted maximum (i.e. each possible pair of data packets from two different sensors has a timestamp difference lower than the predetermined accepted maximum), thereby processing a full set of sensor measurements (i.e. one sensor measurement per sensor) per period with synchronized data packets in order to monitor the body motion of the patient. Preferably, the predetermined accepted maximum is half of a duration of a periodic time base for sending a data packet from said sensors, or half of an approximate period of packet generation of said sensors.

An embodiment comprises repeating, for each received data packet, the calculating of the average of said differences, for a predetermined time duration.

In an embodiment, the predetermined time duration is a sliding time window of predetermined time duration.

An embodiment comprises repeating, for each received data packet, the calculating of the average of said differences, until a convergent result is obtained when said average has variance below a predetermined threshold.

An embodiment comprises outputting periodic data packet sets, wherein each data packet set comprises one received data packet with corrected timestamp for each said embedded wireless data sensor. That is to say, each data packet set comprises one received data packet per embedded wireless data sensor; the data packet received from the first sensor has its timestamp, and the data packets received from the sensors other than the first sensor have the timestamp corrected.

In an embodiment, each said sensor has a periodic time base for sending a data packet for each period from each said sensor.

An embodiment comprises for an individual embedded wireless data sensor, if one data packet has been detected as not received for one sensor period, wherein previous to said period there is an antecedent data packet and following said period there is a subsequent data packet, the steps of:

obtaining the antecedent data packet previous to said period;

waiting and receiving the subsequent data packet following said period;

calculating the interpolation of the sensor measurement between the antecedent data packet and subsequent data packet;

constructing a data packet replacing the data packet which has been detected as not received, having said calculated interpolation of the sensor measurement as the data packet sensor measurement and having said corrected timestamp to synchronize the constructed data packet with the other embedded wireless data sensors.

An embodiment comprises for an individual embedded wireless data sensor, if one or more data packets have been detected as not received for one or more respective sensor periods, wherein previous to said periods there is an antecedent data packet and following said periods there is a subsequent data packet, the steps of:

obtaining the antecedent data packet previous to said periods;

waiting and receiving the subsequent data packet following said periods;

obtaining the sensor measurement of said antecedent data packet and the sensor measurement of said subsequent data packet;

constructing a data packet or packets, each replacing the data packet or packets which have been detected as not received, by calculating the interpolation of the sensor measurement between the antecedent data packet and subsequent data packet for each said data packet or packets which have been detected as not received, and by constructing a data packet or packets replacing each data packet or packets which have been detected as not received, having said calculated interpolation of the sensor measurement as the data packet sensor measurement and using said corrected timestamp to synchronize the constructed data packet or packets with the other embedded wireless data sensors.

In an embodiment, the sensor measurement is an angle and calculating the interpolation for a single constructed data packet comprises calculating the average angle between the antecedent data packet angle and the subsequent data packet angle, in particular the average angle being the minimum rotation vector between said antecedent data packet angle and the subsequent data packet angle.

An embodiment comprises for an individual embedded wireless data sensor, if one or more data packets have been detected as not received for one or more respective sensor periods, wherein previous to said period there is an antecedent data packet and following said period there is not a subsequent data packet, the steps of:

obtaining the antecedent data packet previous to said period;

obtaining the sensor measurement of said antecedent data packet;

constructing a data packet or packets, each replacing the data packet or packets which have been detected as not received, by repeating the obtained antecedent data packet sensor measurement, having said corrected timestamp to synchronize the constructed data packet or packets with the other embedded wireless data sensors.

In an embodiment, the sensor measurement is an angle coded as a quaternion.

An embodiment comprises after an initialization phase, when the timestamps of the received data packets of each embedded wireless data sensor are being corrected, discarding all previously acquired data packets from the embedded wireless data sensors.

An embodiment comprises after an initialization phase, when the timestamps of the received data packets of each embedded wireless data sensor are being corrected, correcting all previously acquired data packets from the embedded wireless data sensors with corrected timestamps to synchronize said data packets from the embedded wireless data sensors.

An embodiment comprises for an individual embedded wireless data sensor, if a data packet has been detected as having a corrected timestamp which has a difference of more than half the duration of said periodic time base in respect of the maximum corrected timestamps of the most recent data packet of the remaining embedded wireless data sensors, discarding said detected data packet.

It is also disclosed a device for synchronizing data packets from embedded wireless data sensors for monitoring body motion of a patient, comprising an electronic data processor configured for carrying out any of the disclosed methods.

Non-transitory storage media including program instructions for implementing a method for synchronizing data packets from embedded wireless data sensors for monitoring body motion of a patient, the program instructions including instructions executable to carry out any of the disclosed methods.

BRIEF DESCRIPTION OF THE DRAWINGS

The following figures provide preferred embodiments for illustrating the disclosure and should not be seen as limiting the scope of invention.

DETAILED DESCRIPTION

The present disclosure relates to a method and device for synchronizing timestamped data packets from embedded data sensors monitoring body motion of a patient, in particular data packets transmitted by a Bluetooth protocol by embedded data sensors monitoring body motion of a patient.

The present disclosure for synchronizing data packets has the following properties:

Data packets are received with a period, for example, of about 20 ms;

The device normally does not receive a data packet from a given tracker older than the last received packet from that tracker.

However, data packets do not have synchronized timestamps, only an internal timestamp, different for each tracker. Moreover, packets are not alternately received, i.e., the device may receive a plurality of packets, for example four packets from one tracker, followed by two packets from another tracker, etc.

In an embodiment, FIG. 1 illustrates steps of an embodiment of the disclosure for synchronized data packets from a plurality of trackers, for example 4 trackers, in order to correctly assess the patient's movements, which is explained in further detail below.

Figure 1A:
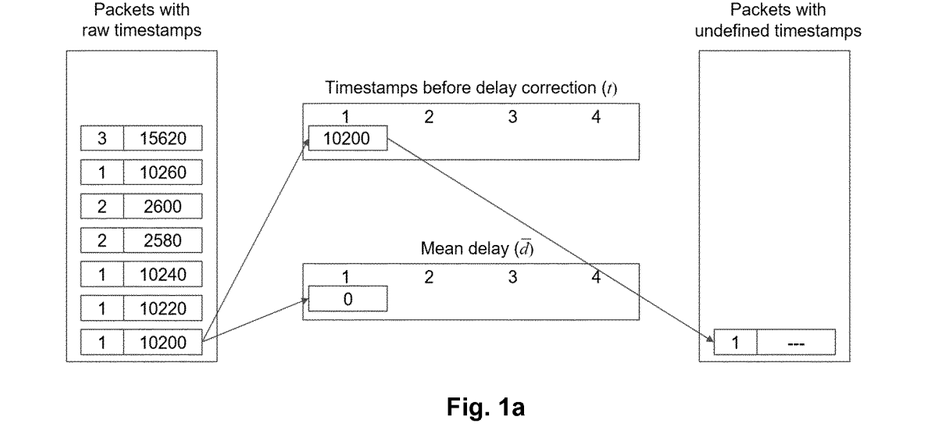
FIG. 1: Schematic representation of steps of an embodiment of the disclosure method.
Figure 1B:
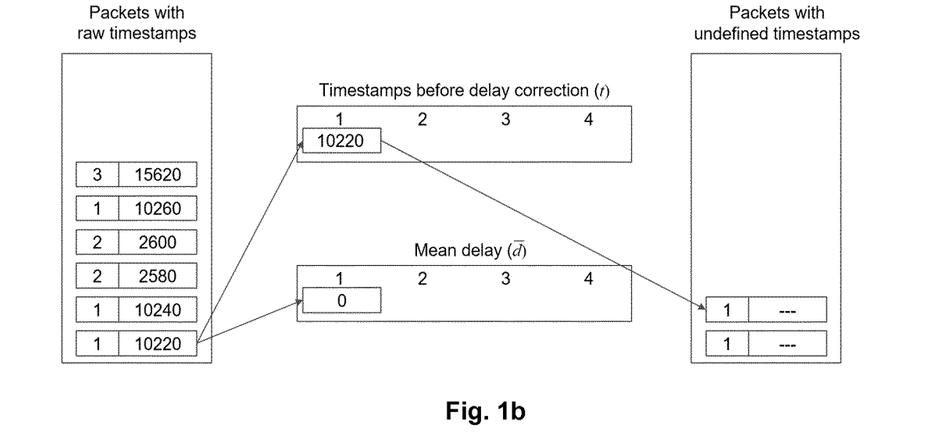
Figure 1C:
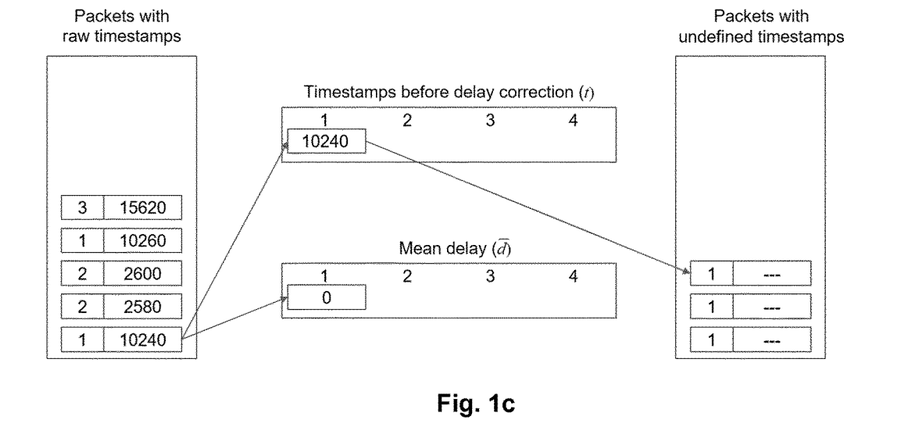
Figure 1D:
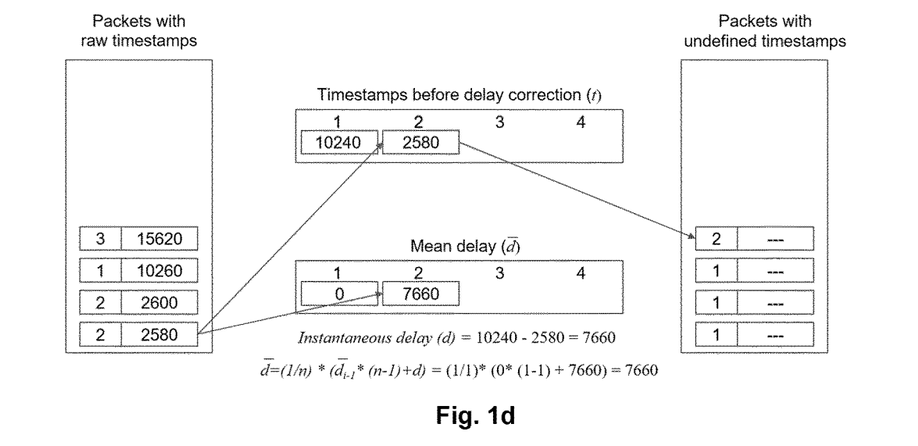
Figure 1E:
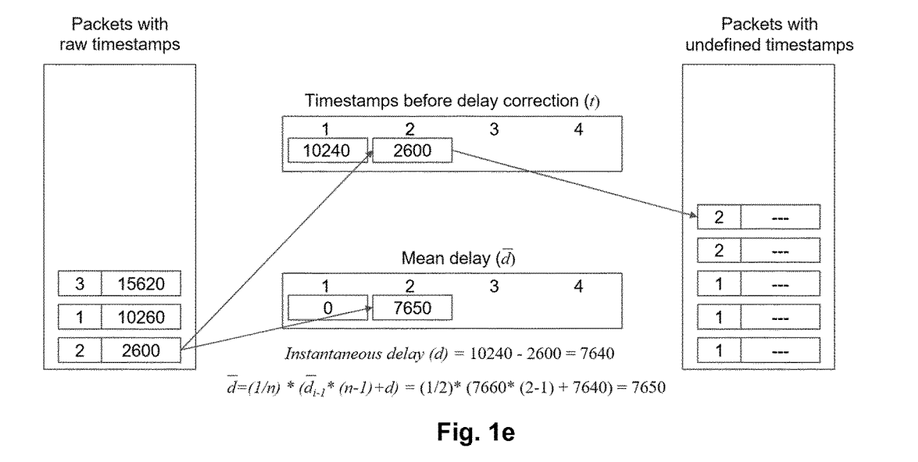
Figure 1F:
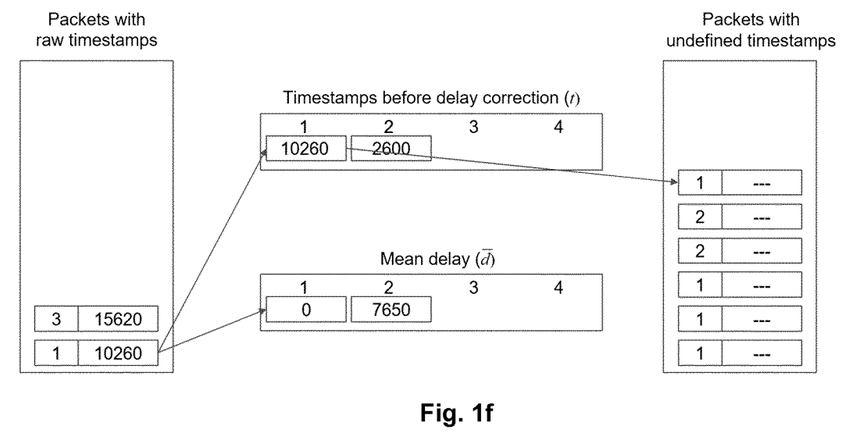
Figure 1G:
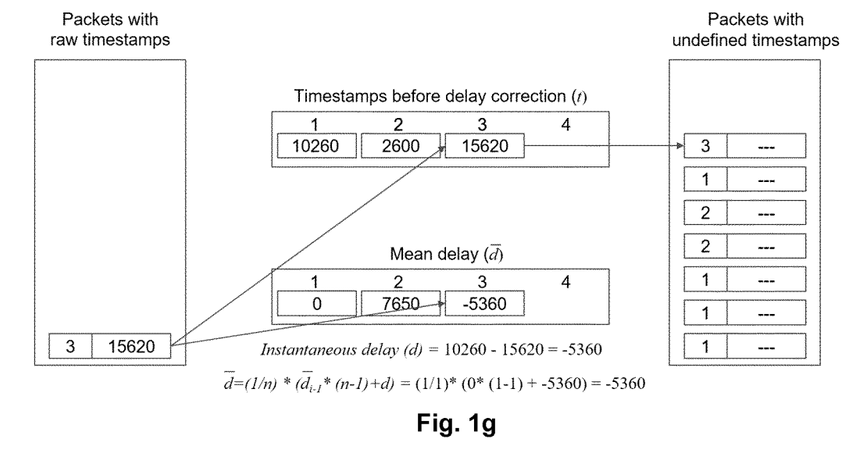
Figure 1H:
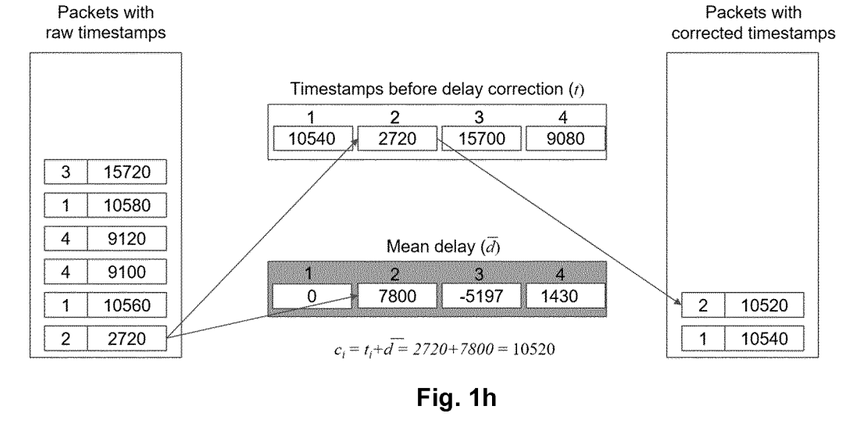
Figure 2:
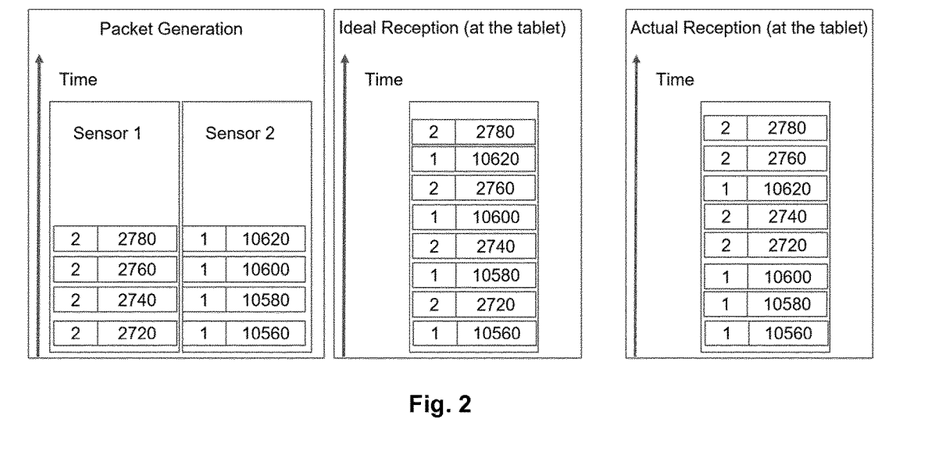
FIG. 2: Schematic representation of an embodiment where is illustrate the problem illustration.

FIG. 2 presents an illustration of the problem addressed by the disclosure. Packets are generated with an approximately constant period but are received in bursts. The order between packets from all trackers is not maintained, but the order of the packets within each tracker is maintained during reception—see also FIG. 3.

Figure 3:
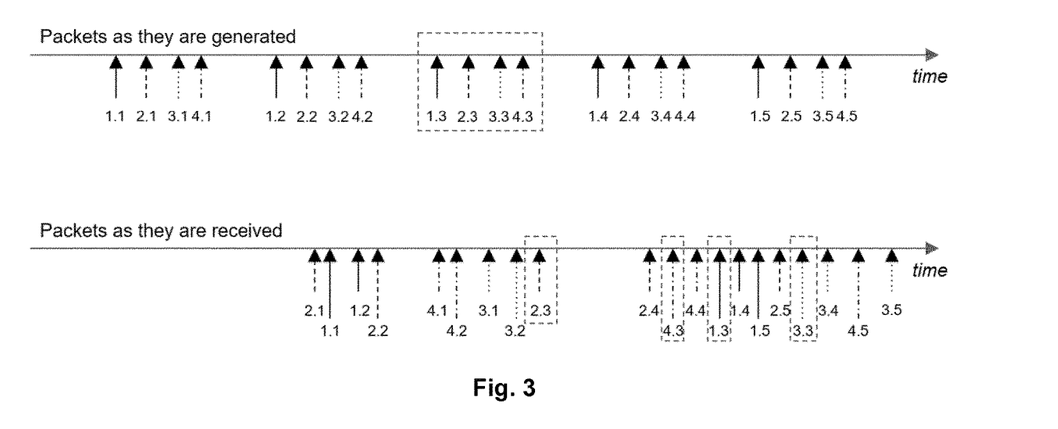
FIG. 3: Schematic representation of an embodiment where is illustrate the problem description.

In FIG. 3, an embodiment is shown of several orientation packet generators (trackers) and a single packet receiver (for example, a tablet) that is responsible for packet processing. The packet receiver needs synchronized data packets from the different trackers in order to correctly assess human motion for rehabilitation purposes in real time. An embodiment has the following properties:

Data packets are generated by each tracker with a period, for example, of about 20 ms.

Data packets are received by the receiver device in bursts, so the period of about 20 ms (for example) is not maintained during reception.

The receiver device normally does not receive a packet from a given tracker older than the last received packet from that same tracker.

Data packets, in an embodiment, contain a quaternion (4 real values that describe a rotation).

Data packets come with a timestamp (internal to each tracker), hereafter defined as raw timestamp. This raw timestamp may be used to know the time interval between two generated packets (between the time instants where they were created), but the raw timestamps from different trackers do not have synchronization.

Trackers normally do not start sending data packets to the tablet at the same time.

Some data packets may not be received (e.g. connection problems).

Figure 4:
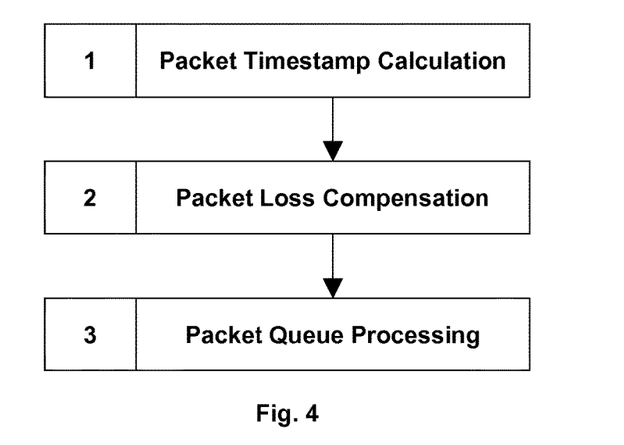
FIG. 4: Schematic representation of an embodiment where is illustrate the process in receiver device.
Figure 5:
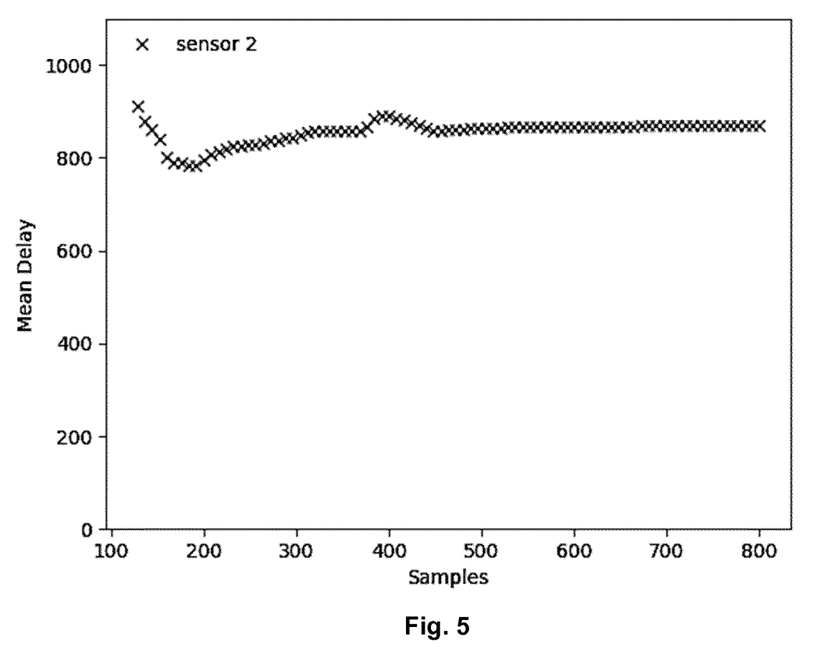
FIG. 5: Illustration of results of an embodiment with two sensors, where sensor "1" is used as the reference first sensor and sensor "2" time base is to be corrected. The graph values illustrate the calculated average of said timestamp differences which is used to correct the timestamps of the received packets.
Figure 6:
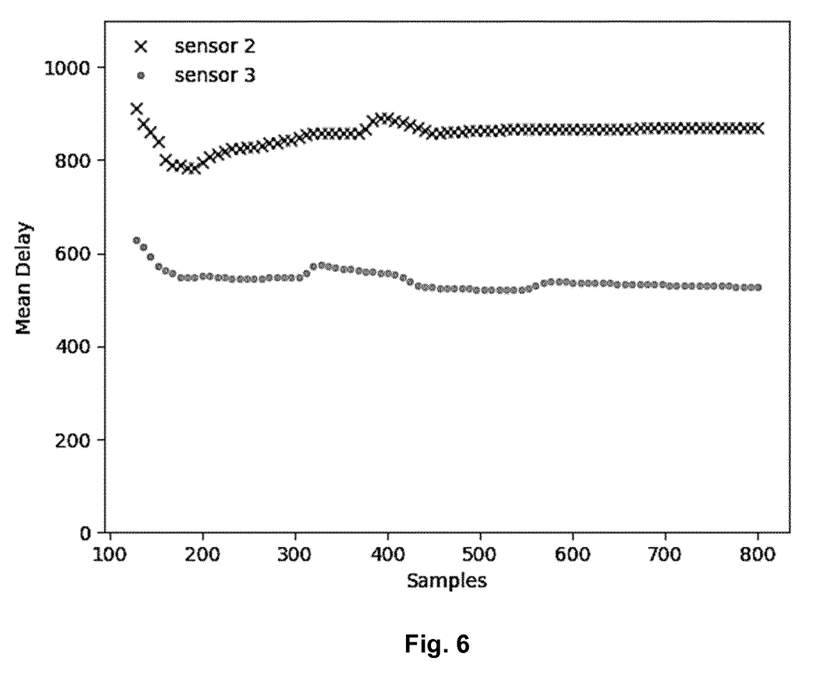
FIG. 6: Illustration of results of an embodiment with three sensors, where sensor "1" is used as the reference first sensor and sensors "2" and "3" time base are to be corrected. The graph values illustrate the calculated averages of said timestamp differences which are used to correct the timestamps of the received packets.

FIG. 4 illustrates an embodiment where the receiver device process may be divided in 3 blocks:

Packet Timestamp Calculation: When a data packet is received, its timestamp is estimated taking into account its generator, its raw timestamp and the last received packet from that generator.

Packet Loss Compensation: Based on the estimated timestamp, data packet loss compensation may be needed.

This block includes possibly data packet orientation interpolation to compensate for mild packet loss (mild loss compensation).

Packet Queue Processing: After timestamp estimation and mild packet loss compensation, data packets are forwarded to queues. Depending on the queue state, packets may be duplicated to compensate for severe packet loss (severe loss compensation). Sampling frequency differences compensation may need to be performed.

In an embodiment of the disclosure, a data packet timestamp estimation can be divided in two parts. The first one occurs before the receiver device has the minimum amount of data packets to perform a good estimation of the delay between timestamps from different trackers. During this period, the output timestamp is defined as invalid and sent to the next block (undefined timestamp). However, the raw timestamps of these packets are used to perform an initial estimation and its value is used to improve the estimation of the mean delay between timestamps from different trackers.

The tracker whose initial packet is received first by the tablet becomes the reference tracker. All the mean delays are calculated with respect to this tracker.

When the first packet of a given tracker is received, the raw timestamp is used as the zero reference for that tracker. Whenever a packet is received, its timestamp is calculated based on the last information available for that tracker (raw timestamp and estimated timestamp):

$$t_0 = 0$$

$$t_i = t_{i-1} + (r_i - r_{i-1})$$

where $t_i$ is the current timestamp estimation, $t_{i-1}$ is the estimated timestamp of the last received packet from the same tracker and $r_i$ and $r_{i-1}$ are the current raw timestamp and the raw timestamp of the last received packet, respectively.

Moreover, the difference of its timestamp when compared to the last received packet from the reference tracker is defined as its current timestamp delay. Mean delay for a given tracker is calculated with the average:

$$\underline{d_i} = (\underline{d_{i-1}} * (n-1) + d) * 1/n,$$

where $\underline{d_i}$ is the current mean delay, $\underline{d_{i-1}}$ is the last mean delay estimation, n is the number of received packets of that tracker and d is the current time difference to the reference tracker. Optionally, this average may be weighted, for example, giving less weight to older values.

When the device has received a predefined number of packets from each tracker, timestamp estimations with the mean delay correction can now be performed (corrected timestamp). The corrected timestamp is calculated by the sum of the current timestamp with the estimated mean delay for that tracker:

$c_i = t_i + \underline{d}$, where $c_i$ is the corrected timestamp, $t_i$ is the current timestamp and $\underline{d}$ the mean delay.

If the device still does not have an estimation for the mean delay between trackers, packets are received by the next block with undefined timestamp. Since there are initial setup steps that may be performed without packet synchronization, the information is processed whenever there is one packet from every tracker.

When the first packet with a defined timestamp is received, all queues are cleared and the packet is pushed to the corresponding queue.

After that, only packets with defined timestamps are pushed to the queues.

When a packet is received its timestamp is compared to the last received packet. If the timestamp difference $\Delta_t$ is greater than $$\frac{3}{2}T$$

(30 ms), the device assumes that at least one packet was lost. However, since packets are being received again, this is classified as a mild packet loss. In this case, the number of lost packets is estimated by:

$$n_l = \left\lfloor \frac{\Delta_t}{T} \right\rfloor - 1$$

where $n_l$ is the number of lost packets, $\Delta_t$ is the timestamp difference between the last queued packet and the current packet and T the approximate period of packet generation. After the number of lost packets is determined, artificial (or interchangeably, dummy or constructed) packets are created to be pushed to the corresponding queue before the received packet is pushed. This is preferred to maintain the orientation processing synchronized.

In an embodiment, orientation is received by means of a quaternion [reference]:

$$q = w + xi + yj + zk$$

$$q = \cos\frac{\theta}{2} + (u_x i + u_y j + u_z k)\sin\frac{\theta}{2}$$

When dummy packets are created, their orientation information is interpolated so that the part of the motion that was lost is better estimated. This is performed by initially defining which quaternion $q_r$ is responsible for a rotation that starts with an orientation corresponding to the last received quaternion $q_{i-1-n_l}$ and leads to the orientation corresponding to the current quaternion $q_i$ [reference]:

$$q_r = q_i q_{i-1-n_l}^{-1}$$

Since the orientation information described with quaternions does not have direct physical meaning, there is a first step to convert a quaternion to a rotation with a defined axis u and angle θ [reference]:

$$\theta = 2a\cos w$$

$$u_x = \frac{x}{\sqrt{1-w^2}}$$

$$u_y = \frac{y}{\sqrt{1-w^2}}$$

$$u_z = \frac{z}{\sqrt{1-w^2}}$$

The results of these operations represent only one possible rotation, there is another possibility which is given by the opposite rotation vector and the supplementary angle, i.e.:

$$\theta = 2\pi - 2a\cos w$$

$$u_x = -\frac{x}{\sqrt{1-w^2}}$$

$$u_y = -\frac{y}{\sqrt{1-w^2}}$$

$$u_z = -\frac{z}{\sqrt{1-w^2}}$$

Since, the movements under analysis are human rehabilitation movements, we use the assumption that the rotation should be the minimum possible, and so the choice becomes the one which leads to the minimum θ. Then, artificial packets are created assuming a constant angular velocity, i.e., the total angle value θ is divided by the number of artificial packets so that each packet contributes with an equal amount of rotation:

$$\Delta_\theta = \frac{\theta}{n_l + 1}$$

where $\Delta_\theta$ is the rotation angle increment for each artificial packet. With this angle, an increment quaternion $q_\Delta$ is defined using the mentioned equation:

$$q_\Delta = \cos\frac{\Delta_\theta}{2} + (u_x i + u_y j + u_z k)\sin\frac{\Delta_\theta}{2}$$

Finally, the orientation quaternion of each artificial packet is given by:

$$q_{a_1} = q_\Delta q_{i-1-n_l}$$

$$q_{a_i} = q_\Delta q_{a_{i-1}}, \text{ for } i=2, \ldots, n_l$$

Trackers do not generate their packets with exactly the same period, there are bias and random errors associated with each tracker. This means that in long term, a tracker may generate more or less packets than the remaining trackers. Therefore, if the device processes the packets every time there is one packet from each tracker, at some point in time, the device will be processing packets corresponding to different points in time.

In an embodiment, to solve this problem, sampling frequency compensation is applied. The principle is that two packets with a time difference of more than $$\frac{1}{2}T$$

do not correspond to the same time instant, and so they should not be processed together. Note that it is acceptable that the trackers have a time difference up to $$\frac{1}{2}T,$$

since their packet generation is not synchronized.

When there is one packet from each tracker to process, the device first peeks the timestamps of these packets. All timestamp values are compared to the maximum timestamp value of the group of timestamps. If all timestamp differences are lower than the accepted maximum $$\left(\frac{1}{2}T\right),$$

the group of packets is processed.

If a certain packet has a timestamp difference greater than the accepted maximum $$\left(\frac{1}{2}T\right),$$

the packet is discarded and the device does not process this group of packets because they do not belong to the same time instant. The remaining packets are kept in the queue.

After the packets are removed, the device starts the process to check if the new group of packets can be processed.

It may be the case where a certain tracker starts losing packets constantly, blocking the process of motion assessment. Even though there is some probability of motion assessment errors because of the lacking information of that tracker, the device tries to continue the motion assessment in real time. In an embodiment, this is done by using the last received orientation of that tracker to estimate its current orientation.

In an embodiment, the receiver monitors continuously the difference of the number of trackers in each queue. When a queue has a difference of number of packets greater than a predefined value when compared to the queue with the greater number of packets, dummy packets are generated and added to this queue.

These dummy packets have their orientation copied from the last received packet of that tracker. Their timestamp is estimated by adding T to last estimated timestamp.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

It is to be appreciated that certain embodiments of the disclosure as described herein may be incorporated as code (e.g., a software algorithm or program) residing in firmware and/or on computer useable medium having control logic for enabling execution on a computer system having a computer processor, such as any of the servers described herein. Such a computer system typically includes memory storage configured to provide output from execution of the code which configures a processor in accordance with the execution. The code can be arranged as firmware or software, and can be organized as a set of modules, including the various modules and algorithms described herein, such as discrete code modules, function calls, procedure calls or objects in an object-oriented programming environment. If implemented using modules, the code can comprise a single module or a plurality of modules that operate in cooperation with one another to configure the machine in which it is executed to perform the associated functions, as described herein.

The disclosure should not be seen in any way restricted to the embodiments described and a person with ordinary skill in the art will foresee many possibilities to modifications thereof. The above described embodiments are combinable. The following claims further set out particular embodiments of the disclosure.

The above-mentioned references should be considered herewith incorporated in their entirety.

The invention claimed is:

1. A method for synchronizing data packets from embedded wireless data sensors for monitoring body motion of a patient, wherein each said sensor has an independent time base for applying timestamps to data packets sent from each said sensor with a respective sensor measurement; said method comprising the steps of:
   receiving, by a device comprising an electronic data processor, an initial data packet having a timestamp from a sensor herewith defined as first sensor;
   receiving, by the device, data packets having a timestamp from said sensors;
   storing, by the device, the timestamp of the initial data packet from the first sensor, herewith defined as reference timestamp;
   for each received data packet from said first sensor, the data packet having a timestamp, and wherein said data packet is received subsequently to said initial data packet:
   the device storing the timestamp of the most recent data packet from said first sensor, herewith defined as subsequent timestamp;
   for each received data packet from the sensors other than the first sensor, the data packet having a timestamp, and wherein said data packet is received subsequently to said initial data packet:
   the device calculating a difference between each subsequent timestamp of a received data packet and the reference timestamp; the device calculating an average of said differences for the received data packets for each said sensor; and the device correcting the timestamp of the received data packet with the calculated average of said differences of the respective sensor when a predefined number of data packets from each respective sensor have been received;
   using, by the device, the corrected timestamps of the received data packets to synchronize the data packets from the embedded wireless data sensors so that the device processes a data packet from each of the sensors wherein the data packet has a timestamp difference, with respect to the data packets from the other sensors, that is lower than a predetermined accepted maximum.

2. A method according to claim 1, further comprises repeating, for each received data packet, the calculating of the average of said differences, for a predetermined time duration.

3. A method according to claim 2, wherein the predetermined time duration is a sliding time window of predetermined time duration.

4. A method according to claim 1, further comprises repeating, for each received data packet, the calculating of the average of said differences, until a convergent result is obtained when said average has variance below a predetermined threshold.

5. A method according to claim 1, further comprising outputting periodic data packet sets, wherein each data packet set comprises one received data packet for each said embedded wireless data sensor, wherein each received data packet for the sensors other than the first sensor has a corrected timestamp.

6. A method according to claim 1, wherein each said sensor has a periodic time base for sending a data packet for each period from each said sensor.

7. A method according to claim 6, further comprising for an individual embedded wireless data sensor, when one or more data packets have been detected by the device as not received for one or more respective sensor periods, wherein previous to said periods there is an antecedent data packet and following said periods there is a subsequent data packet, the device carrying out the steps of:
   obtaining the antecedent data packet previous to said periods;
   waiting and receiving the subsequent data packet following said periods;
   obtaining the sensor measurement of said antecedent data packet and the sensor measurement of said subsequent data packet;
   constructing a data packet or packets, each replacing the data packet or packets which have been detected as not received, by calculating the interpolation of the sensor measurement between the antecedent data packet and subsequent data packet for each said data packet or packets which have been detected as not received, and by constructing a data packet or packets replacing each data packet or packets which have been detected as not received, having said calculated interpolation of the sensor measurement as the data packet sensor measurement and using said corrected timestamp to synchronize the constructed data packet or packets with the other embedded wireless data sensors.

8. A method according to claim 7, wherein the sensor measurement is an angle and calculating the interpolation for a single constructed data packet comprises calculating the average angle between the antecedent data packet angle and the subsequent data packet angle, in particular the average angle being the minimum rotation vector between said antecedent data packet angle and the subsequent data packet angle.

9. A method according to claim 6, further comprising for an individual embedded wireless data sensor, when one or more data packets have been detected by the device as not received for one or more respective sensor periods, wherein previous to said periods there is an antecedent data packet and following said periods there is not a subsequent data packet, the device carrying out the steps of:
   obtaining the antecedent data packet previous to said period;
   obtaining the sensor measurement of said antecedent data packet;
   constructing a data packet or packets, each replacing the data packet or packets which have been detected as not received, by repeating the obtained antecedent data packet sensor measurement, having said corrected timestamp to synchronize the constructed data packet or packets with the other embedded wireless data sensors.

10. A method according to claim 1, further comprising after an initialization phase, when the timestamps of the received data packets of each embedded wireless data sensor are being corrected,
    the device discarding all previously acquired data packets from the embedded wireless data sensors.

11. A method according to claim 1, further comprising after an initialization phase, when the timestamps of the received data packets of each embedded wireless data sensor are being corrected,
    the device correcting all previously acquired data packets from the embedded wireless data sensors with corrected timestamps to synchronize said data packets from the embedded wireless data sensors.

12. A method according to claim 6, further comprising for an individual embedded wireless data sensor, when a data packet has been detected by the device as having a corrected timestamp which has a difference of more than half the duration of said periodic time base in respect of the maximum corrected timestamps of the most recent data packet of the remaining embedded wireless data sensors, the device discarding said detected data packet.

13. A method according to claim 1, wherein the predetermined accepted maximum is half of a duration of a periodic time base for sending a data packet from said sensors, or half of an approximate period of packet generation of said sensors.

14. A device for synchronizing data packets from embedded wireless data sensors for monitoring body motion of a patient, the device comprising an electronic data processor at least performing the following:
  receive an initial data packet having a timestamp from a sensor herewith defined as first sensor;
  receive data packets having a timestamp from said sensors;
  store the timestamp of the initial data packet from the first sensor, herewith defined as reference timestamp;
  for each received data packet from said first sensor, the data packet having a timestamp, and wherein said data packet is received subsequently to said initial data packet:
  store the timestamp of the most recent data packet from said first sensor, herewith defined as subsequent timestamp;
  for each received data packet from the sensors other than the first sensor, the data packet having a timestamp, and wherein said data packet is received subsequently to said initial data packet:
  calculate a difference between each subsequent timestamp of a received data packet and the reference timestamp; calculate an average of said differences for the received data packets for each said sensor; and correct the timestamp of the received data packet with the calculated average of said differences of the respective sensor when a predefined number of data packets from each respective sensor have been received;
  use the corrected timestamps of the received data packets to synchronize the data packets from the embedded wireless data sensors so that the device processes a data packet from each of the sensors wherein the data packet has a timestamp difference, with respect to the data packets from the other sensors, that is lower than a predetermined accepted maximum.

15. A non-transitory storage media including program instructions for implementing a method for synchronizing data packets from embedded wireless data sensors for monitoring body motion of a patient, the program instructions including instructions executable to cause a device at least to:
  receive an initial data packet having a timestamp from a sensor herewith defined as first sensor;
  receive data packets having a timestamp from said sensors;
  store the timestamp of the initial data packet from the first sensor, herewith defined as reference timestamp;
  for each received data packet from said first sensor, the data packet having a timestamp, and wherein said data packet is received subsequently to said initial data packet:
  store the timestamp of the most recent data packet from said first sensor, herewith defined as subsequent timestamp;
  for each received data packet from the sensors other than the first sensor, the data packet having a timestamp, and wherein said data packet is received subsequently to said initial data packet:
  calculate a difference between each subsequent timestamp of a received data packet and the reference timestamp; calculate an average of said differences for the received data packets for each said sensor; and correct the timestamp of the received data packet with the calculated average of said differences of the respective sensor when a predefined number of data packets from each respective sensor have been received;
  use the corrected timestamps of the received data packets to synchronize the data packets from the embedded wireless data sensors so that the device processes a data packet from each of the sensors wherein the data packet has a timestamp difference, with respect to the data packets from the other sensors, that is lower than a predetermined accepted maximum.

16. The device according to claim 14, wherein the electronic data processor further performs repeating, for each received data packet, the calculating of the average of said differences, for a predetermined time duration.

17. The device according to claim 16, wherein the predetermined time duration is a sliding time window of predetermined time duration.

18. The device according to claim 14, wherein the electronic data processor further performs repeating, for each received data packet, the calculating of the average of said differences, until a convergent result is obtained when said average has variance below a predetermined threshold.

19. The device according to claim 14, wherein the electronic data processor further performs outputting periodic data packet sets, wherein each data packet set comprises one received data packet for each said embedded wireless data sensor, wherein each received data packet for the sensors other than the first sensor has a corrected timestamp.

20. The device according to claim 14, wherein for an individual embedded wireless data sensor, when one or more data packets have been detected by the electronic data processor as not received for one or more respective sensor periods, wherein previous to said periods there is an antecedent data packet and following said periods there is a subsequent data packet, the electronic data processor further performs the following:
  obtain the antecedent data packet previous to said periods;
  wait and receive the subsequent data packet following said periods;
  obtain the sensor measurement of said antecedent data packet and the sensor measurement of said subsequent data packet; and
  construct a data packet or packets, each replacing the data packet or packets which have been detected as not received, by calculating the interpolation of the sensor measurement between the antecedent data packet and subsequent data packet for each said data packet or packets which have been detected as not received, and by constructing a data packet or packets replacing each data packet or packets which have been detected as not received, having said calculated interpolation of the sensor measurement as the data packet sensor measurement and using said corrected timestamp to synchronize the constructed data packet or packets with the other embedded wireless data sensors.

* * * * *